ized Search Report dated Apr. 21, 2015 issued in PCT/

United States Patent
Tsuruta et al.

(10) Patent No.: US 9,874,739 B2
(45) Date of Patent: Jan. 23, 2018

(54) OPTICAL FIBER SCANNER, ILLUMINATION APPARATUS, AND OBSERVATION APPARATUS

(71) Applicant: OLYMPUS CORPORATION, Tokyo (JP)

(72) Inventors: Hiroshi Tsuruta, Hachioji (JP); Yasuaki Kasai, Hachioji (JP); Yoshiro Okazaki, Hachioji (JP); Hirokazu Yokota, Hachioji (JP); Kazutoshi Kumagai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 63 days.

(21) Appl. No.: 15/199,254

(22) Filed: Jun. 30, 2016

(65) Prior Publication Data

US 2016/0377857 A1    Dec. 29, 2016

Related U.S. Application Data

(63) Continuation of application No. PCT/JP2015/052819, filed on Feb. 2, 2015.

(30) Foreign Application Priority Data

Feb. 26, 2014    (JP) .................................. 2014-035654

(51) Int. Cl.
  *G02B 23/24* (2006.01)
  *G02B 23/26* (2006.01)
  (Continued)

(52) U.S. Cl.
  CPC ...... *G02B 23/2469* (2013.01); *A61B 1/00096* (2013.01); *A61B 1/00172* (2013.01);
  (Continued)

(58) Field of Classification Search
  CPC ............ G02B 23/2469; G02B 23/2484; G02B 26/103
  (Continued)

(56) References Cited

U.S. PATENT DOCUMENTS 6,004,499 A * 12/1999 Bishop .................. B29C 70/543
                                                    204/157.42
2004/0254474 A1   12/2004 Seibel et al.
  (Continued)

FOREIGN PATENT DOCUMENTS

JP    2001-327460 A    11/2001
JP    2008-504557 A     2/2008
  (Continued)

OTHER PUBLICATIONS

International Search Report dated Apr. 21, 2015 issued in PCT/JP2015/052819.
  (Continued)

*Primary Examiner* — Seung C Sohn
(74) *Attorney, Agent, or Firm* — Scully, Scott, Murphy & Presser, P.C.

(57) ABSTRACT

This optical fiber scanner has an elongated optical fiber, a vibration transmission member which has a column-like shape and has a penetrating hole through which the optical fiber penetrates, and a piezoelectric element provided on an outer surface of the vibration transmission member, wherein the penetrating hole is a fitted hole which is formed from a proximal end of the vibration transmission member to a middle of the vibration transmission member and the optical fiber is fitted, and the penetrating hole is an accommodation hole which is formed from the middle to a distal end of the vibration transmission member, which has a large inner diameter than an outer diameter of the optical fiber, and which accommodates a distal end portion of the optical fiber (Continued)

with a gap between the optical fiber and the accommodation hole.

8 Claims, 9 Drawing Sheets

(51) Int. Cl.
*G02B 26/10* (2006.01)
*A61B 1/00* (2006.01)
*A61B 1/07* (2006.01)

(52) U.S. Cl.
CPC ............ *A61B 1/07* (2013.01); *G02B 23/2484* (2013.01); *G02B 23/26* (2013.01); *G02B 26/103* (2013.01)

(58) Field of Classification Search
USPC .................................................. 250/227.26
See application file for complete search history.

(56) References Cited

U.S. PATENT DOCUMENTS

| 2006/0195014 | A1 | 8/2006 | Seibel et al. |
| 2007/0299309 | A1 | 12/2007 | Seibel et al. |
| 2008/0249369 | A1 | 10/2008 | Seibel et al. |
| 2015/0205050 | A1* | 7/2015 | Funakubo ............ G02B 26/101 385/25 |

FOREIGN PATENT DOCUMENTS

| JP | 2008-531193 A | 8/2008 |
| JP | 2010-523198 A | 7/2010 |
| WO | WO 2006/004743 A2 | 1/2006 |
| WO | WO 2006/093655 A2 | 9/2006 |
| WO | 2008/123859 A1 | 10/2008 |

OTHER PUBLICATIONS

Japanese Office Action dated Sep. 5, 2017 in Japanese Patent Application No. 2014-035654.

* cited by examiner

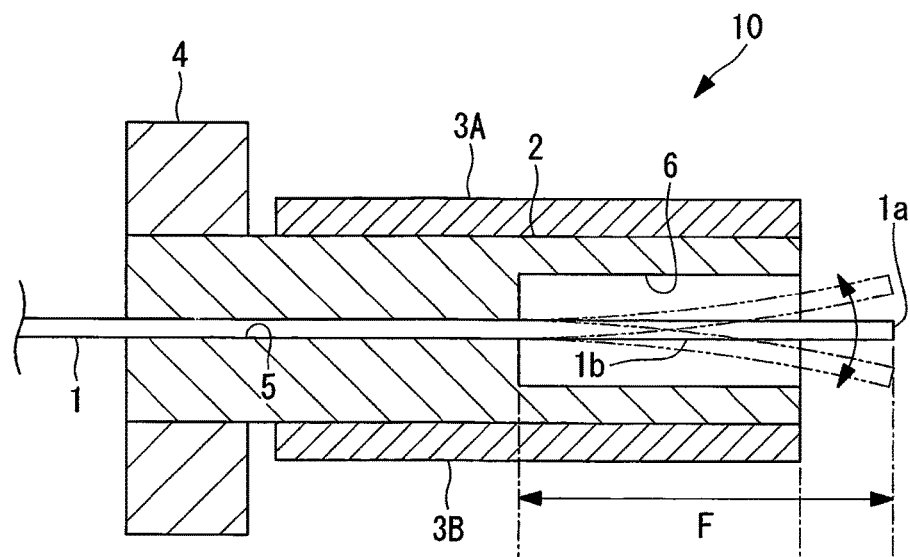
FIG. 7A
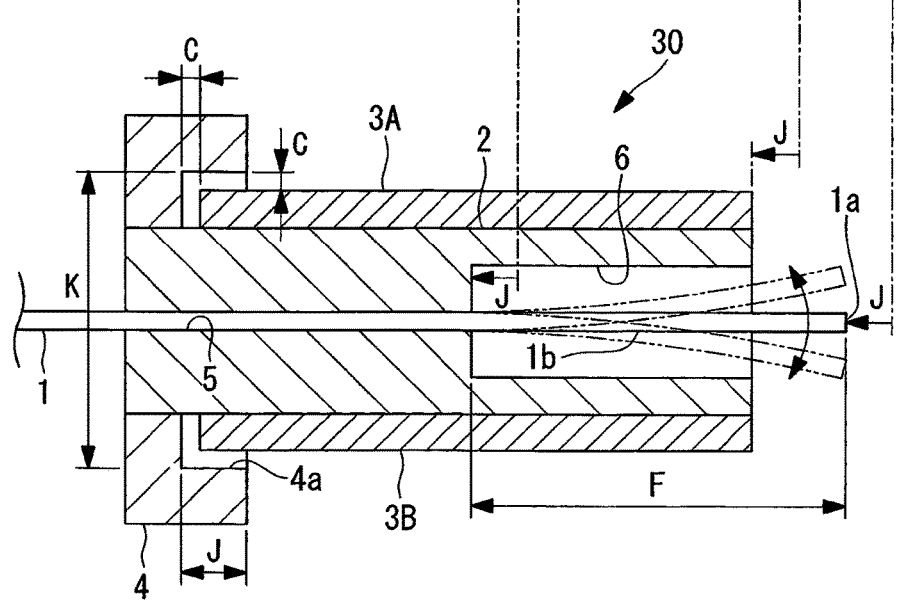
FIG. 7B
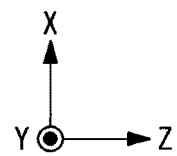

OPTICAL FIBER SCANNER, ILLUMINATION APPARATUS, AND OBSERVATION APPARATUS

CROSS-REFERENCE TO RELATED APPLICATIONS

This application is a Continuation Application of International Application No. PCT/JP2015/052819 filed on Feb. 2, 2015, which claims priority to Japanese Application No. 2014-035654 filed on Feb. 26, 2014. The contents of International Application No. PCT/JP2015/052819 and Japanese application No. 2014-035654 are incorporated herein by reference in its entirety.

TECHNICAL FIELD

The present invention relates to an optical fiber scanner, an illumination apparatus, and an observation apparatus.

BACKGROUND ART

There are known optical fiber scanners in which the light emitted from the distal end of the optical fiber is scanned along a spiral track by making the distal end of the optical fiber vibrate at high speed (for example, see PTL 1). In the optical fiber scanner disclosed in PTL 1, a cylindrical lead-zirconate-titanate (PZT) actuator supports the optical fiber in a cantilever state, and the distal end, which is protruded from the actuator, of the optical fiber is vibrated.

CITATION LIST

Patent Literature

{PTL 1} Japanese Unexamined Patent Application, Publication No. 2008-504557

SUMMARY OF INVENTION

A first aspect of the present invention is an optical fiber scanner comprising: an elongated optical fiber which is capable of guiding light and emitting the light from a distal end thereof; a vibration transmission member which has a column-like shape along a longitudinal direction of the optical fiber and which has a penetrating hole through which the optical fiber penetrates; and a piezoelectric element provided on an outer peripheral surface of the vibration transmission member, for generating bending vibration in the vibration transmission member in a direction which crosses a longitudinal direction of the optical fiber by means of vibrating with expanding and contracting of the element in the longitudinal direction by applying alternating voltage, wherein the penetrating hole comprises a fitted hole which is formed from a proximal end surface of the vibration transmission member to a middle portion of the vibration transmission member in the longitudinal direction and to which an outer peripheral surface of the optical fiber is fitted, and an accommodation hole which is formed from the middle portion to a distal end surface of the vibration transmission member, which has an inner diameter larger than an outer diameter of the optical fiber, and which accommodates a distal end portion of the optical fiber so that a gap between the outer peripheral surface of the optical fiber and the accommodation hole is formed.

DESCRIPTION OF EMBODIMENTS

First Embodiment

An optical fiber scanner 10 according to a first embodiment of the present invention will be described below with reference to FIGS. 1A to 5B. Note that an orthogonal coordinate system X, Y, and Z are used in the following explanation, and also X direction and Y direction thereof correspond to the radial direction of the optical fiber 1, and Z direction thereof corresponds to the longitudinal direction of the optical fiber 1.

Figure 1A:
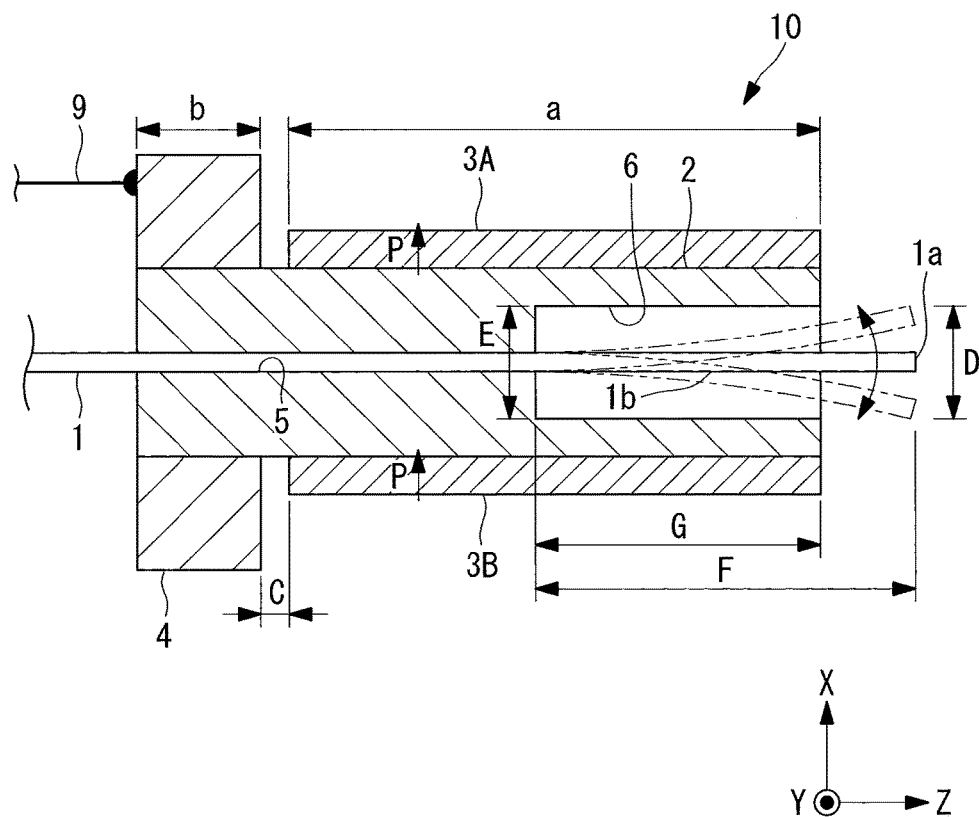
FIG. 1A is a longitudinal sectional view showing a configuration of an optical fiber scanner according to a first embodiment of the present invention.
Figure 1B:
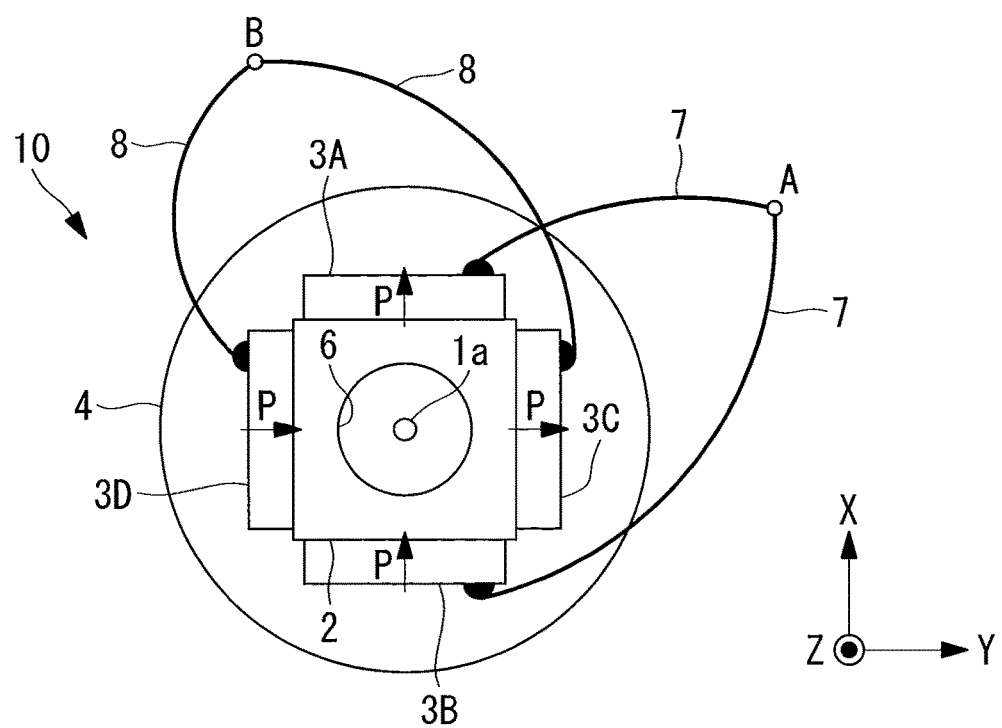
FIG. 1B is a front view showing the optical fiber scanner of FIG. 1A seen from the tip end side of an optical fiber.

As shown in FIGS. 1A and 1B, the optical fiber scanner 10 according to this embodiment has an elongated round rod-like optical fiber 1 made of a glass material, a vibration transmission member 2 directed toward the outer peripheral surface of the distal end portion of the optical fiber 1, a plate-like piezoelectric element 3A, 3B, 3C, 3D provided on the outer peripheral surface of the vibration transmission member 2, and a support member 4.

The vibration transmission member 2 is a quadrangular prism composed of a metal material such as nickel or copper, and structurally reinforce the flexible optical fiber 1. The vibration transmission member 2 has the penetrating hole 5, 6 configured to penetrate along the center axis thereof in the longitudinal direction from the distal end surface to the proximal end surface, and the optical fiber 1 penetrates the penetrating hole 5, 6. The penetrating hole is composed of the fitted hole 5 and the accommodation hole 6.

The fitted hole 5 has an inner diameter which is substantially the same as the outer diameter of the optical fiber 1, and extends from the proximal end surface of the vibration transmission member 2 to a middle position thereof. The outer peripheral surface of the optical fiber 1, which is to be fitted to the fitted hole 5, is fitted in the inner peripheral surface of the fitted hole 5, and thereby the optical fiber 1 is supported by the fitted hole 5 in a cantilever state.

The accommodation hole 6 has an inner diameter which is larger than the outer diameter of the optical fiber 1, and extends from said middle position to the distal end surface. A portion (which is called as "distal end vibration portion 1*b*" in the following explanation) of the optical fiber 1, which is protruded from the distal end opening of the fitted hole 5 opening at the bottom surface of the accommodation hole 6, is accommodated in the accommodation hole 6 so as to form a cylindrical gap between the optical fiber 1 and the inner peripheral surface of the accommodating hole 6. The diameter E of the accommodating hole 6 is slightly greater than the maximum amplitude (the maximum value of the whole amplitude) in the X and Y directions of the distal end 1*a* of the optical fiber 1 that vibrates by driving the piezoelectric elements 3A, 3B, 3C, 3D as described later. The depth G of the accommodating hole 6 is equal to or less than the length F of the distal end vibration portion, and the distal end 1*a* of the optical fiber 1 is disposed at a position which is the same position as or a slightly protruded position from the distal end surface of the vibration transmission member 2.

The piezoelectric elements 3A, 3B, 3C, 3D are made of a piezoelectric material, such as lead-zirconate-titanate (PZT), and plate-like members having the length a. Each of the front surfaces and the rear surfaces of the piezoelectric elements 3A, 3B, 3C, 3D are treated by an electrode processing such that the front surface serves as a positive pole, and the rear surface serves as a negative pole. As a result, polarization from the positive poles to the negative poles as shown by the arrow P is formed in the piezoelectric elements 3A, 3B, 3C, 3D. The thickness directions, which is the polarization direction P, of the piezoelectric elements 3A, 3B, 3C, 3D are the radial direction of the optical fiber 1, and the piezoelectric elements 3A, 3B, 3C, 3D are attached to the four side surfaces of the vibration transmission member 2, respectively, using electrically conductive adhesive. Gaps C are formed between the piezoelectric elements 3A, 3B, 3C, 3D and the support member 4.

In this configuration, two piezoelectric elements 3A, 3B which face each other in the X direction are attached to the vibration transmission member 2 such that the polarization directions P thereof are the same. Lead wires 7 for driving the piezoelectric elements are connected to the piezoelectric elements 3A, 3B by an electrically conductive adhesive. When alternating voltage of the A phase is applied to the piezoelectric elements 3A, 3B through the lead wires 7, the piezoelectric elements 3A, 3B expand and contract to vibrate in Z direction which is perpendicular to the polarization direction P. In this situation, when one of the two piezoelectric elements 3A, 3B contracts in Z direction and the other expands in Z direction, bending vibration in X direction is caused. When the bending vibration in X direction caused in the vibration transmission member 2 is transmitted to the optical fiber 1, bending vibration in X direction occurs in the distal end vibration portion 1*a* inside the accommodation hole 6.

Similarly, two piezoelectric elements 3C, 3D which face each other in the Y direction are also attached to the vibration transmission member 2 such that the polarization directions P thereof are the same. Lead wires 8 for driving the piezoelectric elements are connected to the piezoelectric elements 3C, 3D by an electrically conductive adhesive. When alternating voltage of the B phase is applied to the piezoelectric elements 3C, 3D through the lead wires 8, the piezoelectric elements 3C, 3D expand and contract to vibrate in Z direction which is perpendicular to the polarization direction P. In this situation, when one of the two piezoelectric elements 3C, 3D contracts in Z direction and the other expands in Z direction, bending vibration in Y direction is caused. When the bending vibration in Y direction caused in the vibration transmission member 2 is transmitted to the optical fiber 1, bending vibration in Y direction occurs in the distal end vibration portion 1*a* inside the accommodation hole 6.

The support member 4 is a member for fixing a middle portion of the optical fiber 1 to an outer tube 12 of an observation apparatus 100 described below. The support member 4 is made of a metal material such as stainless steel, and a cylindrical member having the length b. The support member 4 is fitted on the outer peripheral surface of the proximal end portion of the vibration transmission member 2 and fixed to the vibration transmission member 2 by an electrically conductive adhesive. In this configuration, the support member 4 serves as a common ground (GND) when driving the piezoelectric elements 3A, 3B, 3C, 3D by the alternating voltage. This is why the GND lead 9 for driving the piezoelectric elements is connected to the surface of the holding member 4 by an electrically conductive adhesive. Note that the leads 7, 8, 9 are not shown in FIGS. 2 to 7.

Next, the function of the optical fiber scanner 10 configured as described above will be explained below. In order to scan illumination light, which is supplied to the optical fiber 1 from a light source, on a specimen, an alternating voltage of the phase A with a frequency which produces the bending vibration state (mode) with a maximum amplitude of the distal end 1*a* of the optical fiber 1 is applied to the piezoelectric elements 3A and 3B through the lead wires 7. By this, the bending vibration in a linear way in X direction is caused in the distal end vibration portion 1*b* of the optical fiber 1.

Similarly, an alternating voltage of the phase B with a frequency which produces the bending vibration state (mode) with a maximum amplitude of the distal end 1*a* of the optical fiber 1 is applied to the piezoelectric elements 3C and 3D through the lead wires 8. By this, the bending vibration in a linear manner in Y direction is caused in the distal end vibration portion 1*b* of the optical fiber 1.

In this state, when alternating voltages whose phase are shifted by π/2 from each other are simultaneously applied to the piezoelectric elements 3A, 3B and the piezoelectric elements 3C, 3D, the distal end 1*a* of the optical fiber 1 is vibrated along a circular track. Further, when the amplitudes of the two of the alternating voltages are changed along a sign curve, the distal end 1*a* of the optical fiber is vibrated along a spiral track. By this, the illumination light L on the specimen X can be scanned in a two-dimensional manner along a spiral track.

In this situation, in the optical fiber scanner 10 of the present invention, the whole part or the most part of the distal end vibration portion 1*b* of the optical fiber 1 is accommodated in the accommodation hole 6 formed in the distal end side portion of the vibration transmission member 2, and vibrated in the accommodation hole 6. By employing the configuration in which the optical fiber 1 is scarcely protruded from the vibration transmission member 2, the length from the proximal end surface to the distal end 1*a* of the optical fiber 1 becomes short in the optical fiber scanner 10. This portion is disposed at the stiff tip portion of an observation apparatus or an illumination apparatus when the optical fiber 10 is provided in the observation apparatus or the illumination apparatus. Thus, by using the optical fiber scanner 10 of the present invention, it becomes possible to realize an observation apparatus and an illumination apparatus which have a short stiff tip portion.

Next, an observation apparatus 100 having the optical fiber scanner 10 of the present invention will be described below.

Figure 2:
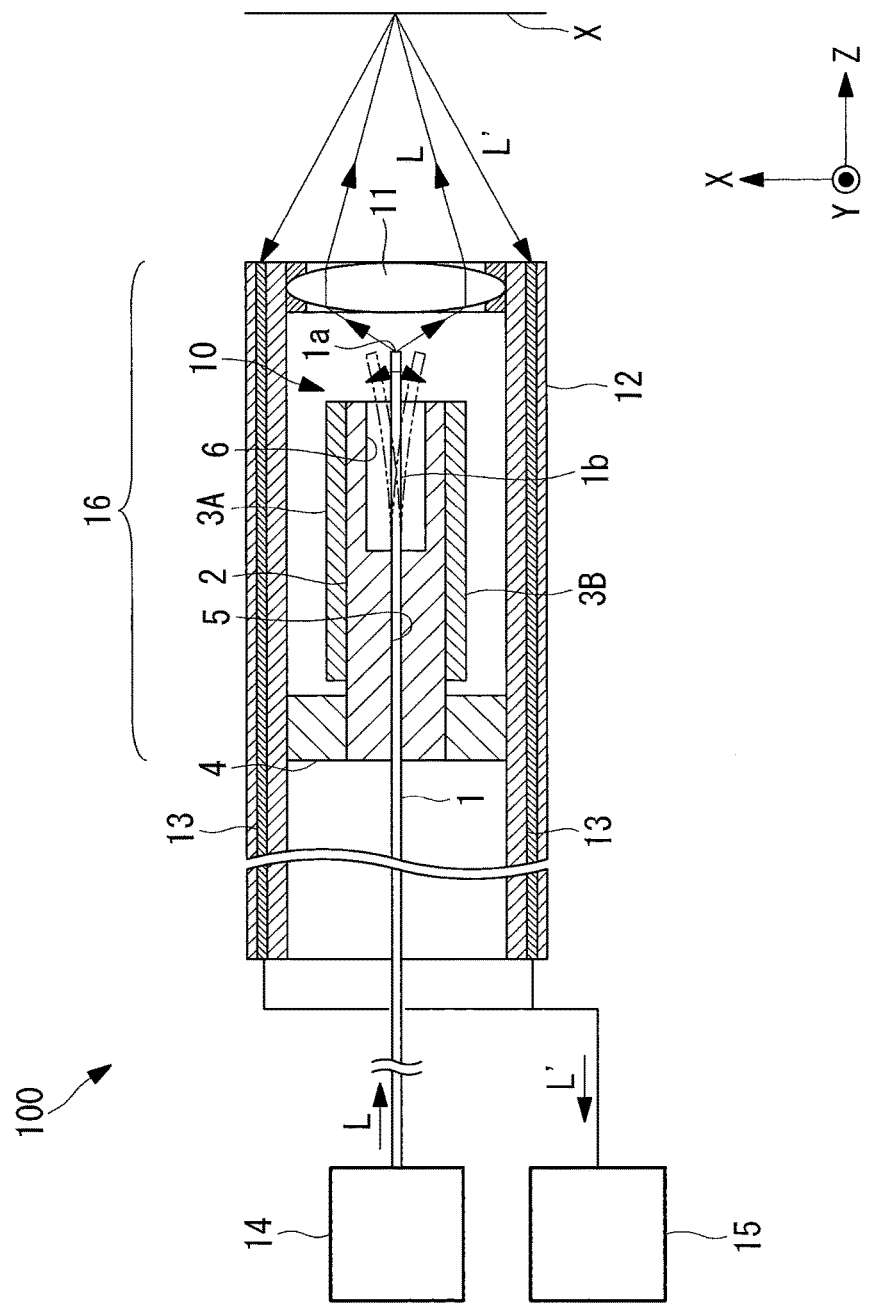
FIG. 2 is a longitudinal sectional view showing configuration of an observation apparatus having the optical fiber scanner of FIG. 1A.

The observation apparatus 100 of the present invention is an apparatus which has probe-like shape as endoscopes are. Also, as shown in FIG. 2, the observation apparatus 100 has an illumination lens 11 disposed at the distal end side of the optical fiber scanner 10, an elongated outer tube 12 for accommodating the optical fiber scanner 10 and an illumination lens 11, a plurality of detection optical fibers 13 arranged in the circumferential direction at the outer side of the optical fiber scanner 10, a light source 14 for supplying illuminating light to the proximal end of the optical fiber 1, and a light detector (light detection portion) 15 which detects the light received by the detection optical fiber 13.

The illumination lens 11 is disposed so that its rear side focal position is positioned at the same position as the distal end 1a of the optical fiber 1. The illumination lens 11 receives light emitted from the distal end 1a of the optical fiber 1, and emits the received illumination light L after converting the illumination light into a parallel light, and thereby the light is focused on the specimen X. Although FIG. 2 shows a single lens as the illumination lens 11, the illumination lens can be composed of a plurality of lenses.

The optical fiber scanner 10 is supported in the outer tube 12 by fixing the outer peripheral surface of the support member 4 and the inner peripheral surface of the outer tube 12 with each other by an epoxy adhesive.

The light source 14 is disposed at a proximal end side of the outer tube 12, and the proximal end of the optical fiber 1 is connected to the light source 14.

The light detector 15 is disposed at a proximal end side of the outer tube 12, and the proximal end of each of the detection optical fibers 13 is connected to the light detector 15.

With the observation apparatus 100 having the aforementioned configuration, the distal end 1a of the optical fiber 1 is vibrated along a spiral track in a state in which the illumination lens faces the specimen X, and then the illumination light L is supplied to the optical fiber 1 from the light source 14, the illumination light L which has gone through the optical fiber 1 is emitted from the distal end 1a. The emitted illumination light L is converged by the illumination lens 11 and emitted to the specimen X, and the irradiated light on the specimen X is scanned in a two-dimensional manner along a spiral track.

The return light L' of the illumination light L from the specimen X is received by the plurality of detection optical fibers 13, and its intensity is detected by the light detector 15. The observation apparatus 100 detects the return light L' by the light detector 15 synchronously with the scanning cycle of the illuminating light L, and forms an image of the specimen X by means of making the detected intensities of the return light L' correspond with the scanned positions.

With the aforementioned configuration, in the observation apparatus 100 of this embodiment, the stiff tip portion 16, which starts from the proximal end surface of the support member 4 to the distal end surface where the illumination lens 11 is disposed, is covered by the stiff outer tube 12. As described above, since the portion of the optical fiber scanner 10 which is disposed in the stiff tip portion 16, it becomes possible to shorten the stiff tip portion 16. By this, it becomes possible to easily move the observation apparatus 100 in a curved portion in a narrow lumen, and therefore it becomes possible to obtain the observation apparatus 100 whose operability is high, which is one of the advantageous points.

Although the observation apparatus 100 has the optical fiber scanner 100 in this embodiment, an observation apparatus can be made so that the apparatus does not have the detection optical fiber 13 and the light detector 15 which are described above, and that the apparatus only has an illumination function.

The optical fiber scanner 10 of this embodiment can be modified as shown in the following first to third modified examples.

Figure 3A:
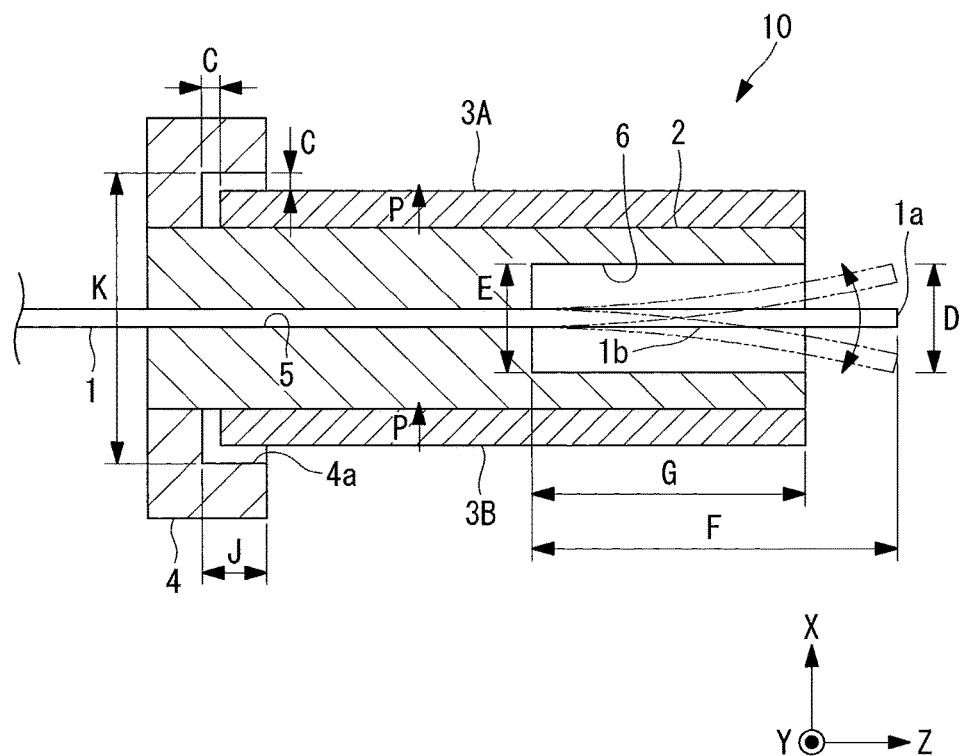
FIG. 3A is a longitudinal sectional view showing a first modified example of the optical fiber scanner of FIG. 1A.
Figure 3B:
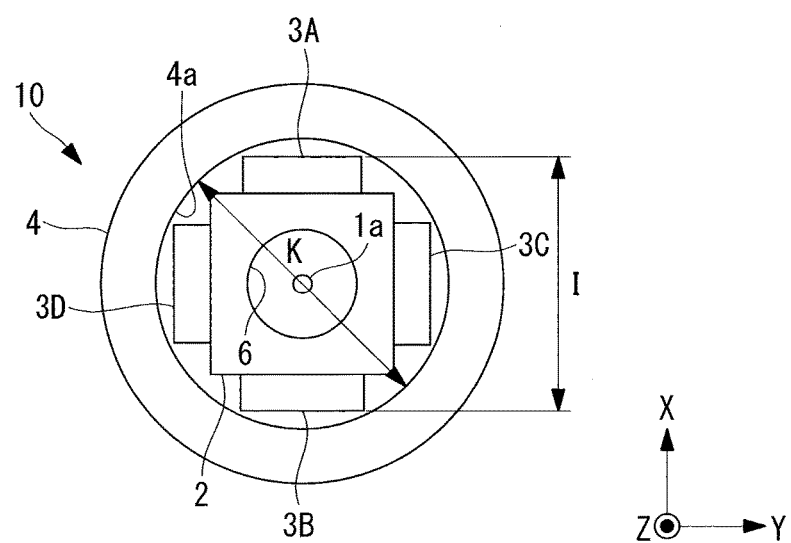
FIG. 3B is a front view showing the optical fiber scanner of FIG. 3A seen from the tip end side thereof.

In the first modified example, as shown in FIGS. 3A and 3B, a counterbore-like recess 4a may be formed in the distal end surface of the support member 4, and the proximal end portions of the piezoelectric elements 3A, 3B, 3C, 3D may be inserted into the recess 4a so that the piezoelectric elements 3A, 3B, 3C, 3D are disposed both of the inside and the outside of the recess 4a. The recess 4a has a diameter K which satisfies the following expression so that a circular gap is formed around the outer surfaces of the proximal end portions of the piezoelectric elements 3A, 3B, 3C, 3D disposed inside the recess 4a. In the following expression, I is a distance between the outer surfaces of the two opposing piezoelectric elements 3A, 3B or a distance between the outer surfaces of the two opposing piezoelectric elements 3C, 3D.

$$K > \sqrt{2} \times I$$

Figure 4A:
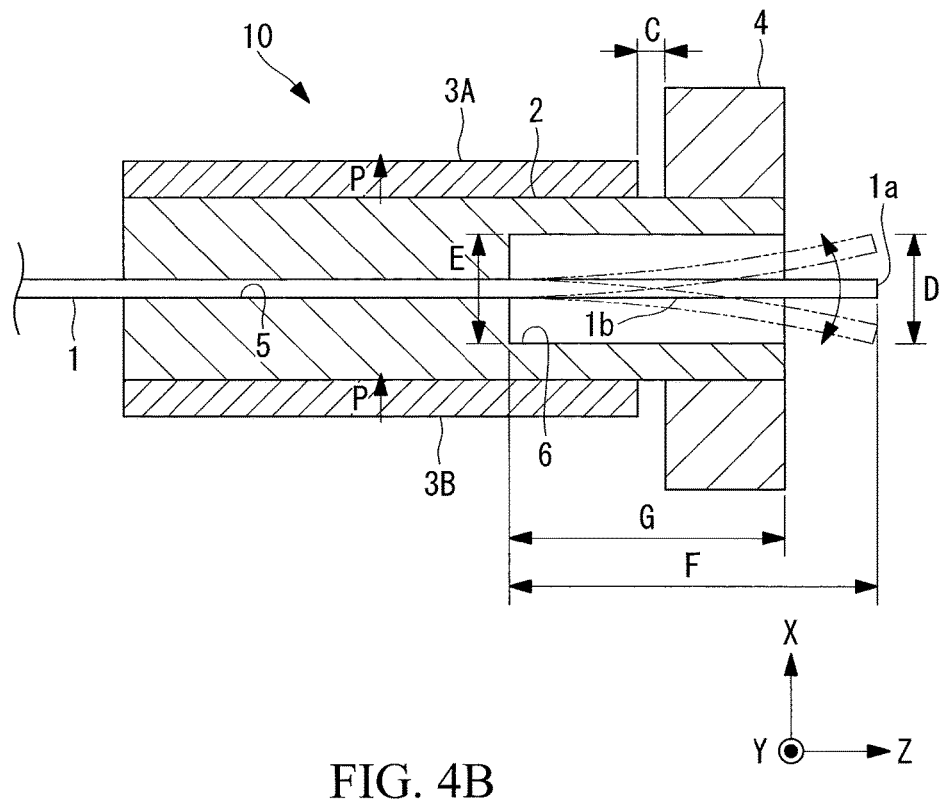
FIG. 4A is a longitudinal sectional view showing a second modified example of the optical fiber scanner of FIG. 1A.
Figure 4B:
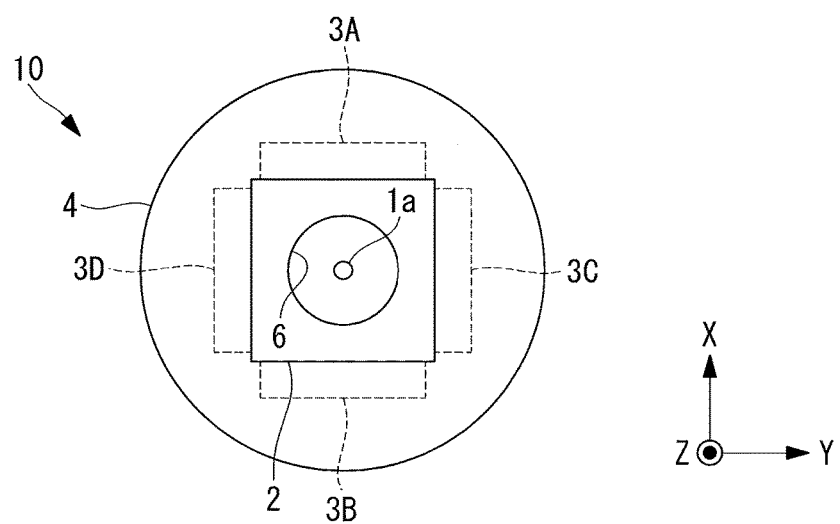
FIG. 4B is a front view showing the optical fiber scanner of FIG. 4A seen from the tip end side thereof.

In the second modified example, as shown in FIGS. 4A and 4B, the positions of the piezoelectric elements 3A, 3B, 3C, 3D and the support member 4 can be reversed. Thus, the support member 4 may be disposed at the distal end side of the vibration transmission member 2, and the piezoelectric elements 3A, 3B, 3C, 3D may be positioned at the proximal end side of the vibration transmission member 2.

Figure 5A:
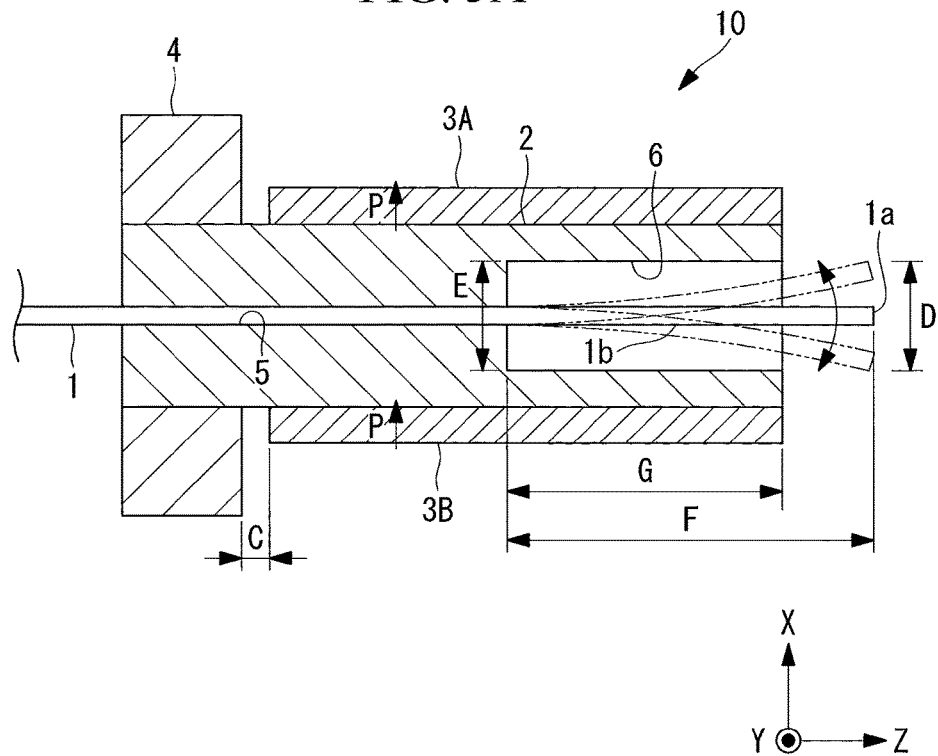
FIG. 5A is a longitudinal sectional view showing a third modified example of the optical fiber scanner of FIG. 1A.
Figure 5B:
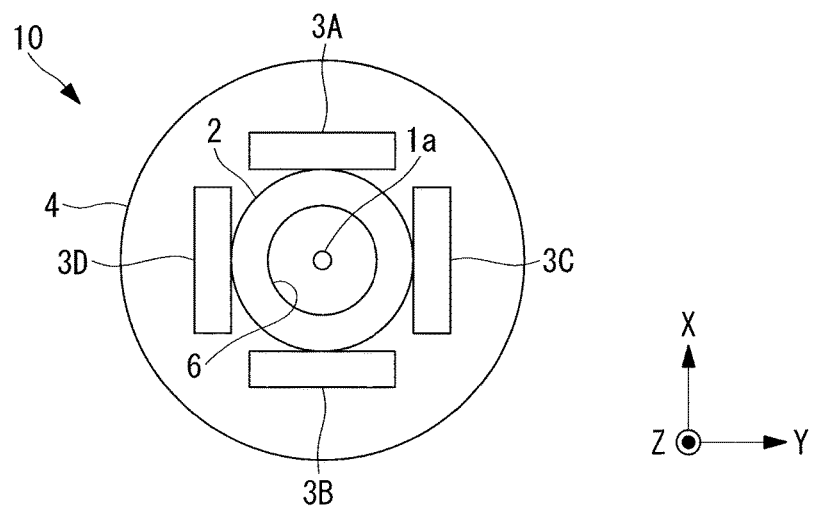
FIG. 5B is a front view showing the optical fiber scanner of FIG. 5A seen from the tip end side thereof.

In the third modified example, as shown in FIGS. 5A and 5B, the vibration transmission member 2 may have a column shape.

Second Embodiment

Next, an optical fiber scanner 20 according to a second embodiment of the present invention will be described below with reference to FIGS. 6A and 6B. Note that the configurations which are different from those of the first embodiment will be mainly explained below in this embodiment, and explanation for the configurations which are also employed in the first embodiments will be omitted, assigning the same reference signs.

Figure 6A:
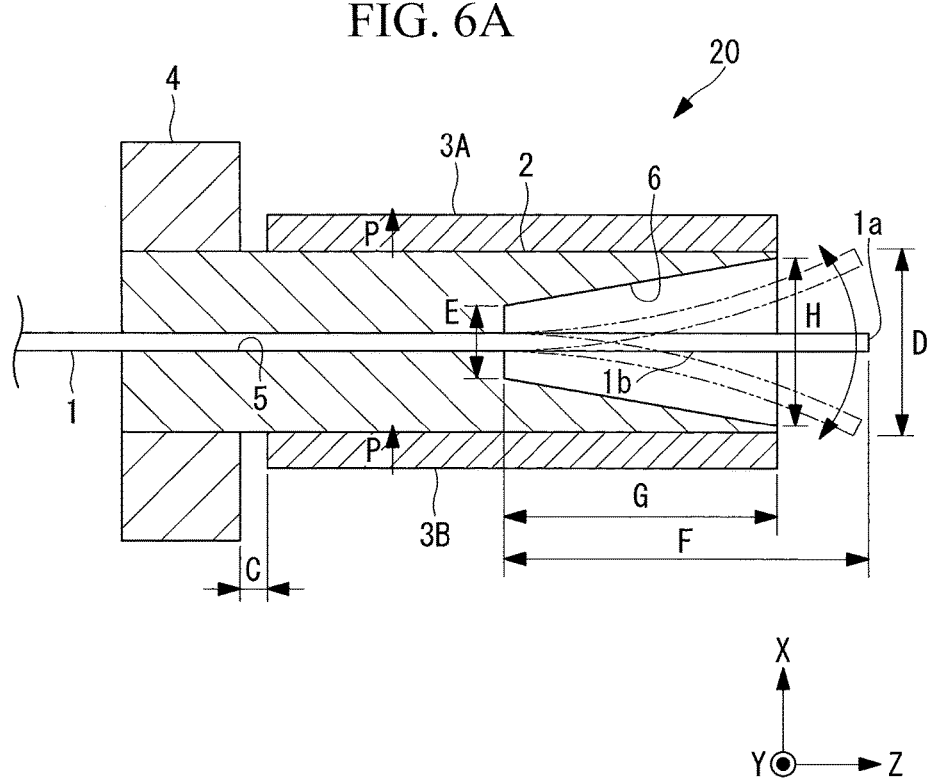
FIG. 6A is a longitudinal sectional view showing a configuration of an optical fiber scanner according to a second embodiment of the present invention.
Figure 6B:
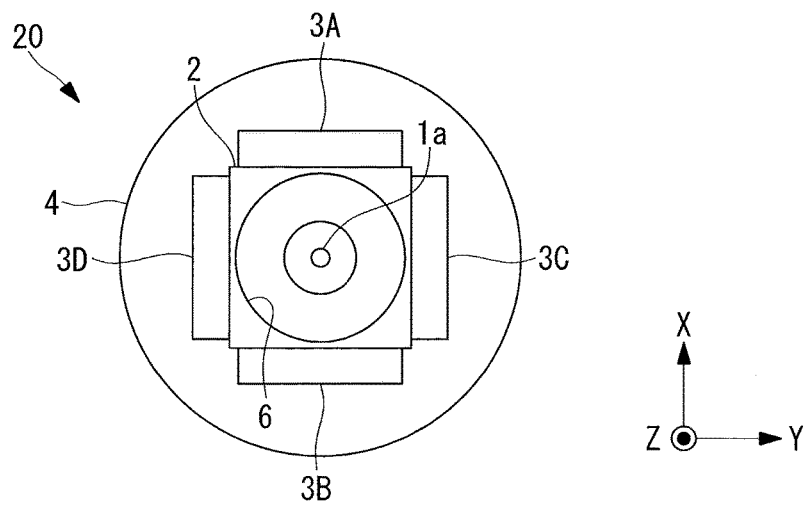
FIG. 6B is a front view showing the optical fiber scanner of FIG. 6A seen from the tip end side thereof.
Figure 7:
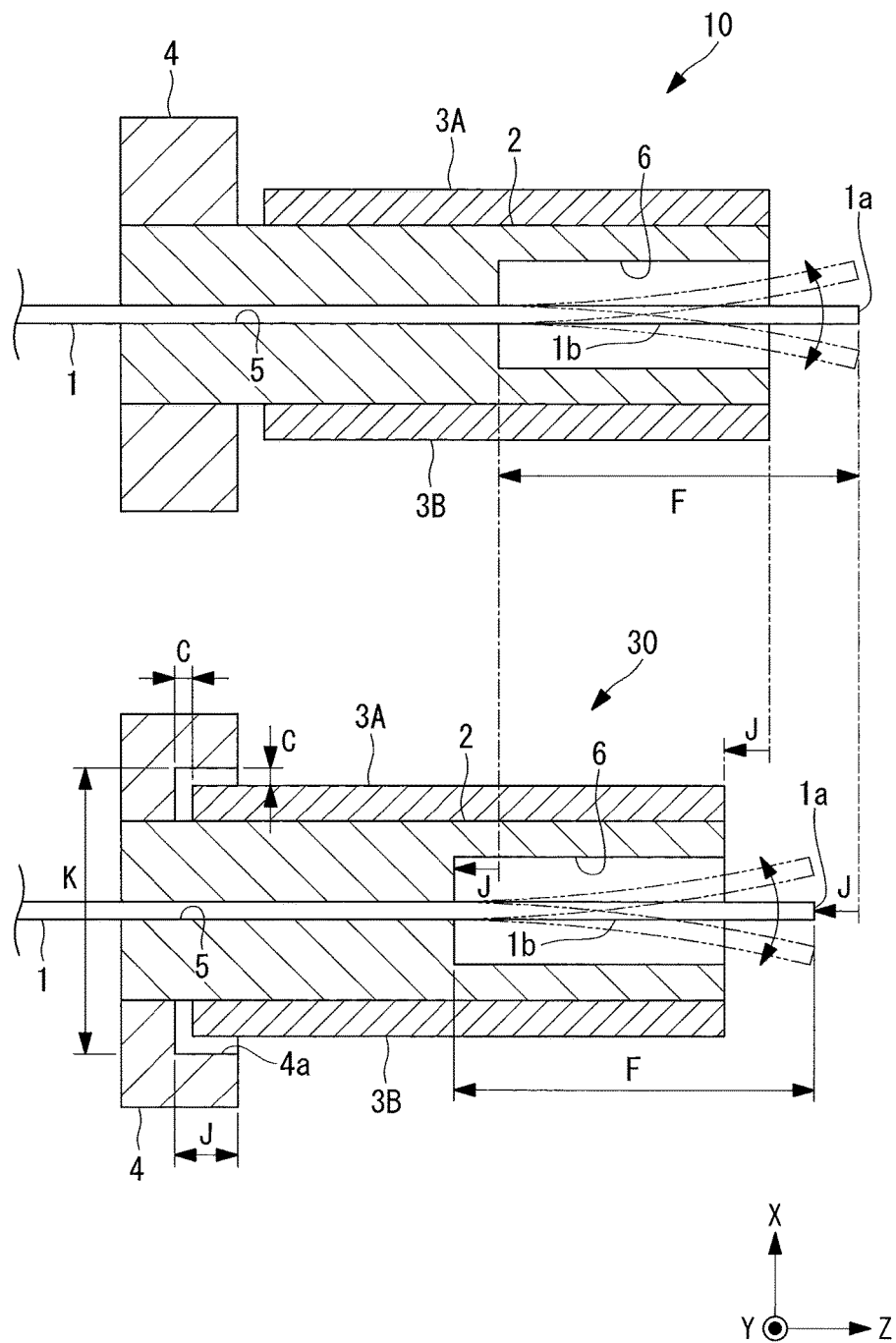
FIG. 7A is a longitudinal sectional view showing a configuration of an optical fiber scanner according to a third embodiment of the present invention.
FIG. 7B is a longitudinal sectional view showing the optical fiber scanner of FIG. 1A.

As shown in FIGS. 6A and 6B, in the optical fiber scanner 20 of this embodiment, the configuration of the accommodation hole 6 is different from that of the first embodiment.

Specifically, as shown in FIG. 6A, the accommodation hole 6 has a truncated-cone shape whose diameter becomes gradually large from the proximal end side to the distal end side of the vibration transmission member 2, and the diameter H of the opening at the distal end surface of the vibration transmission member 2 is greater than the diameter E of the bottom surface.

Since the optical fiber scanner 20 of this embodiment affords effects which are the same as or similar to those of the first embodiment, the explanation is omitted.

With the optical fiber scanner 20 of this embodiment, the amplitude of the distal end vibration portion 1b becomes the maximum at the distal end thereof. Thus, by forming the inner diameter of the accommodation hole 6 in the truncated-cone shape whose diameter becomes the maximum at the distal end thereof, the contact of the distal end vibration portion 1b and the inner circumferential surface of the accommodation hole 6 can be effectively prevented. Also, when the amplitude of the distal end vibration portion 1b is the same, it becomes possible to reduce the outer diameter of the vibration transmission member 2 can be reduced. Further, the outer diameter of the vibration transmission member 2 is the same, it becomes possible to make the amplitude of the distal end 1a of the optical fiber 1 larger, which can make the scanned area by the illumination light L larger. Since this embodiment has other effects which are the same as the first embodiment, those explanations are omitted.

Third Embodiment

Next, an optical fiber scanner 30 according to a third embodiment of the present invention will be described below with reference to FIGS. 7A and 7B. Note that the configurations which are different from those of the first embodiment will be mainly explained below in this embodiment, and explanation for the configurations which are also employed in the first embodiments will be omitted, assigning the same reference signs.

As shown in FIGS. 7A and 7B, the optical fiber scanner 30 of this embodiment is similar to the first modified example of the first embodiment, and the proximal end portions of the piezoelectric elements 3A, 3B, 3C, 3D are inserted into the recess 4a provided in the support member 4. In FIGS. 7A and 7B, for comparison purpose relative to the optical fiber scanner 10 of the first embodiment, the optical fiber scanner which is the same as one of the first embodiment is shown at FIG. 7A, and the optical fiber scanner 30 of this embodiment is shown at FIG. 7B.

In the optical fiber scanner 30, the piezoelectric elements 3A, 3B, 3C, 3D are shifted toward the proximal end side by a distance J which is the same as the depth of the recess 4a. Also, the vibration transmission member 2 is shortened by the length J, and the position of the bottom surface of the accommodation hole 6 is shifted toward the proximal end side by the distance J. Note that the length F of the distal end vibration portion 1b is the same as that of the first embodiment, and therefore the distal end 1a of the optical fiber 1 is shifted toward the proximal end side by the distance J.

Since the optical fiber scanner 20 of this embodiment affords effects which are the same as or similar to those of the first embodiment, the explanation is omitted.

With the optical fiber scanner 30 of this embodiment, by forming the recess 4a in the support member 4, it becomes possible to shift the positions of the piezoelectric elements 3A, 3B, 3C, 3D and the distal end vibration portion 1b toward the proximal end side, maintaining the dimensions of the piezoelectric elements 3A, 3B, 3C, 3D and the proximal end vibration portion 1b, which can make the portion disposed in the stiff tip portion 16 shorter. By employing the configuration, when compared with the optical fiber scanner 10 of the first embodiment, an illumination apparatus and an observation apparatus which have a shorter stiff tip portion 16 can be realized, which is one of the advantageous points.

The inventors have arrived at the following aspects of the invention.

A first aspect of the present invention is an optical fiber scanner comprising: an elongated optical fiber which is capable of guiding light and emitting the light from a distal end thereof; a vibration transmission member which has a column-like shape along a longitudinal direction of the optical fiber and which has a penetrating hole through which the optical fiber penetrates; and a piezoelectric element provided on an outer peripheral surface of the vibration transmission member, for generating bending vibration in the vibration transmission member in a direction which crosses a longitudinal direction of the optical fiber by means of vibrating with expanding and contracting of the element in the longitudinal direction by applying alternating voltage, wherein the penetrating hole comprises a fitted hole which is formed from a proximal end surface of the vibration transmission member to a middle portion of the vibration transmission member in the longitudinal direction and to which an outer peripheral surface of the optical fiber is fitted, and an accommodation hole which is formed from the middle portion to a distal end surface of the vibration transmission member, which has an inner diameter larger than an outer diameter of the optical fiber, and which accommodates a distal end portion of the optical fiber so that a gap between the outer peripheral surface of the optical fiber and the accommodation hole is formed.

According to the first aspect of the present invention, when the alternating voltage is applied to the piezoelectric element and the bending vibration is generated in the vibration transmission member, this bending vibration is transmitted from the portion of the optical fiber which is fitted in the fitted hole to the portion of the optical fiber (distal end vibration portion) which is penetrated toward the distal end side from the fitted hole in a cantilever state, and then the distal end of the optical fiber is vibrated in a direction which crosses the longitudinal direction. By this configuration, it is possible to scan the illumination light emitted from the distal end of the optical fiber in a direction which crosses the light axis of the illumination light In this state, the bending vibration is generated in at least part of the distal end vibration portion of the optical fiber while the distal end vibration portion is accommodated in the accommodation hole which is formed at the distal end side portion of the vibration transmission member, the protruding amount of the optical fiber from the distal end surface of the vibration transmission member becomes small. By this configuration, the portion which is formed from the proximal end surface of the vibration transmission member to the distal end surface of the optical fiber, which corresponds to a stiff tip portion of a probe like an endoscope in which the optical fiber scanner is provided, can be shortened, and therefore the stiff tip portion of the probe can be shortened.

In the first aspect described above, the piezoelectric element may be provided so that the element exits at the both sides relative to the middle portion in the longitudinal direction, and the piezoelectric element may be provided at a position which includes a distal end or an adjacent of the distal end of the vibration transmission member.

By employing these configurations, it becomes possible to efficiently transmit vibration with expanding and contracting of the piezoelectric element to the optical fiber by the vibration transmission member, providing the piezoelectric element so as to effectively utilize the space of the vibration transmission member in the longitudinal direction.

In the first aspect described above, the accommodation hole may be cylindrical and have a diameter which is greater than a maximum amplitude of the distal end of the optical fiber in the direction which crosses the longitudinal direction, and a depth which is the same as or less than a length of a portion of the optical fiber which protrudes from the fitted hole toward the distal end side.

By employing this configuration, it becomes possible to vibrate the distal end vibration portion of the optical fiber in the accommodation hole, without contact between the optical fiber and the inner wall of the accommodation hole.

In the first aspect described above, the accommodation hole may have a truncated-cone shape whose diameter becomes gradually large from the proximal end side to the distal end side.

By employing this configuration, the inner diameter of the accommodation hole becomes greater at the distal end side where the amplitude of the distal end vibration portion becomes greater, and thereby it becomes possible to effectively prevent the contact between the distal end vibration portion and the inner wall of the accommodation portion.

In the first aspect described above, a cylindrical support member which supports an outer peripheral surface of a proximal end portion of the vibration transmission member may be further employed, and the support member may have a recess provided on an end surface at a distal end of the support member, for forming a gap between the outer peripheral surface of the vibration transmission member and the support member, the gap is greater than a dimension of the piezoelectric element in a radial direction of the optical fiber, and also a proximal end portion of the piezoelectric element may be disposed in the recess.

By employing these configurations, the positions of the piezoelectric element, the accommodation hole, and the distal end vibration portion can be shifted to the proximal end side, and thereby the portion formed from the proximal end surface of the vibration transmission member to the distal end surface of the optical fiber can be further shortened.

A second aspect of the present invention is an illumination apparatus comprising: an optical fiber scanner described above; a light source which is disposed at a proximal end side position of the optical fiber scanner and which supplies illumination light to the optical fiber; an illumination lens which is disposed at a distal end side position of the optical fiber scanner and which focuses the light emitted from the distal end of the optical fiber on a specimen; and an elongated outer tube which accommodates the optical fiber scanner and the illumination lens.

A third aspect of the present invention is an observation apparatus comprising: an illumination apparatus described above; and a light detection portion which detects return light which returns from the specimen by irradiation of the light from the illumination apparatus to the specimen.

The aforementioned aspects can afford an advantage of enabling to shorten the stiff tip portion of the probe.

REFERENCE SIGNS LIST 1 optical fiber
1a distal end
1b distal end vibration portion
2 vibration transmission member
3A, 3B, 3C, 3D piezoelectric element
4 support member
5 fitted hole (penetrating hole)
6 accommodation hole (penetrating hole)
7, 8 lead
9 GND lead
10, 20, 30 optical fiber scanner
11 illumination lens
12 outer tube
13 detection optical fiber
14 light source
15 light detector (light detection portion)
16 stiff tip portion
L illumination light
L' return light
X specimen

The invention claimed is:

1. An optical fiber scanner comprising:
an elongated optical fiber which is capable of guiding light and emitting the light from a distal end thereof;
a vibration transmission member which has a column-like shape along a longitudinal direction of the optical fiber and which has a penetrating hole through which the optical fiber penetrates; and
a piezoelectric element provided on an outer peripheral surface of the vibration transmission member, for generating bending vibration in the vibration transmission member in a direction which crosses a longitudinal direction of the optical fiber by means of vibrating with expanding and contracting of the element in the longitudinal direction by applying alternating voltage,
wherein the penetrating hole comprises a fitted hole which is formed from a proximal end surface of the vibration transmission member to a middle portion of the vibration transmission member in the longitudinal direction and to which an outer peripheral surface of the optical fiber is fitted, and an accommodation hole which is formed from the middle portion to a distal end surface of the vibration transmission member, which has an inner diameter larger than an outer diameter of the optical fiber, and which accommodates a distal end portion of the optical fiber so that a gap between the outer peripheral surface of the optical fiber and the accommodation hole is formed.

2. The optical fiber scanner according to claim 1, wherein the piezoelectric element is provided so that the element exits at the both sides relative to the middle portion in the longitudinal direction.

3. The optical fiber scanner according to claim 1, wherein the piezoelectric element is provided at a position which includes a distal end or an adjacent of the distal end of the vibration transmission member.

4. The optical fiber scanner according to claim 1, wherein the accommodation hole is cylindrical and has a diameter which is greater than a maximum amplitude of the distal end of the optical fiber in the direction which crosses the longitudinal direction, and a depth which is the same as or less than a length of a portion of the optical fiber which protrudes from the fitted hole toward the distal end side.

5. The optical fiber scanner according to claim 1, wherein the accommodation hole has a truncated-cone shape whose diameter becomes gradually large from the proximal end side to the distal end side.

6. The optical fiber scanner according to claim 1, further comprising a cylindrical support member which supports an outer peripheral surface of a proximal end portion of the vibration transmission member,
wherein the support member has a recess provided on an end surface at a distal end of the support member, for forming a gap between the outer peripheral surface of the vibration transmission member and the support member, the gap is greater than a dimension of the piezoelectric element in a radial direction of the optical fiber,
wherein a proximal end portion of the piezoelectric element is disposed in the recess.

7. An illumination apparatus comprising:
an optical fiber scanner described in claim 1;

a light source which is disposed at a proximal end side position of the optical fiber scanner and which supplies illumination light to the optical fiber;

an illumination lens which is disposed at a distal end side position of the optical fiber scanner and which focuses the light emitted from the distal end of the optical fiber on a specimen; and an elongated outer tube which accommodates the optical fiber scanner and the illumination lens.

8. An observation apparatus comprising:

an illumination apparatus described in claim 7; and a light detection portion which detects return light which returns from the specimen by irradiation of the light from the illumination apparatus to the specimen.

* * * * *